(12) United States Patent
Wachtel et al.

(10) Patent No.: US 8,267,082 B2
(45) Date of Patent: Sep. 18, 2012

(54) MEDICAMENTS MAGAZINE FOR AN INHALER, AND A MULTI-DOSE POWDER INHALER

(75) Inventors: Herbert Wachtel, Ingelheim am Rhein (DE); Johannes Geser, Ingelheim am Rhein (DE); Burkhard Metzger, Ingelheim am Rhein (DE); Michael Spallek, Ingelheim am Rhein (DE); Michael Krueger, Ingelheim am Rhein (DE); Hubert Kunze, Dortmund (DE); Achim Moser, Chemnitz (DE); Elmar Mock, Colombier (CH); Antonino Lanci, Bern (CH); Andre Klopfenstein, La Neuveville (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 935 days.

(21) Appl. No.: 12/296,877

(22) PCT Filed: Apr. 13, 2007

(86) PCT No.: PCT/CH2007/000180
§ 371 (c)(1),
(2), (4) Date: Dec. 24, 2008

(87) PCT Pub. No.: WO2007/118342
PCT Pub. Date: Oct. 25, 2007

(65) Prior Publication Data
US 2009/0250057 A1 Oct. 8, 2009

(30) Foreign Application Priority Data
Apr. 13, 2006 (EP) ...................................... 06405163

(51) Int. Cl.
*A61M 15/00* (2006.01)

(52) U.S. Cl. .............................. 128/203.21; 128/203.15
(58) Field of Classification Search ............. 128/203.21, 128/203.15, 203.12; 222/83, 83.5
See application file for complete search history.

(56) References Cited

U.S. PATENT DOCUMENTS

| 4,627,432 A | | 12/1986 | Newell et al. |
| 5,048,514 A | * | 9/1991 | Ramella ................... 128/203.21 |
| 5,590,645 A | | 1/1997 | Davies et al. |
| 5,595,175 A | * | 1/1997 | Malcher et al. .......... 128/203.15 |
| 5,642,727 A | | 7/1997 | Datta et al. |
| 5,778,873 A | | 7/1998 | Braithwaite |

(Continued)

FOREIGN PATENT DOCUMENTS

DE 44 00 083 A1 7/1995

(Continued)

*Primary Examiner* — Loan Thanh
*Assistant Examiner* — Sandhara Ganesan
(74) *Attorney, Agent, or Firm* — Michael P. Morris; Wendy A. Petka

(57) ABSTRACT

The invention is a medicament magazine having at least one medicament chamber for use in a powder inhaler, wherein the magazine is formed from two foil strips applied to one another and the at least one medicament chamber is formed between the foil strips as depicted in exemplary FIGS. 1a and 1b. The medicament chambers have an internal structure (3) which comprises in its interior a space for receiving a powdered medicament and stabilizes this inner space against external mechanical influences. In another embodiment in which the internal structure preferably also has a stabilizing function, the structure has means for opening one foil strip. In addition, the medicament chamber contains a retaining device which holds the internal structure on the medicament magazine after the medicament chamber has been opened.

3 Claims, 9 Drawing Sheets

U.S. PATENT DOCUMENTS

| | | | |
|---|---|---|---|
| 5,896,855 A * | 4/1999 | Hobbs et al. | 128/203.15 |
| 6,082,356 A | 7/2000 | Stradella | |
| 6,443,307 B1 | 9/2002 | Burridge | |
| 6,443,367 B1 * | 9/2002 | Bova | 239/276 |
| 6,655,381 B2 | 12/2003 | Keane et al. | |
| 7,401,713 B2 | 7/2008 | Ede et al. | |
| 2006/0157053 A1 * | 7/2006 | Barney et al. | 128/200.23 |

FOREIGN PATENT DOCUMENTS

| | | |
|---|---|---|
| EP | 1 003 478 B1 | 5/2000 |
| WO | 91/06333 A1 | 5/1991 |
| WO | 01/41846 A1 | 6/2001 |
| WO | 2005/002654 A2 | 1/2005 |
| WO | 2005/016424 A2 | 2/2005 |

* cited by examiner

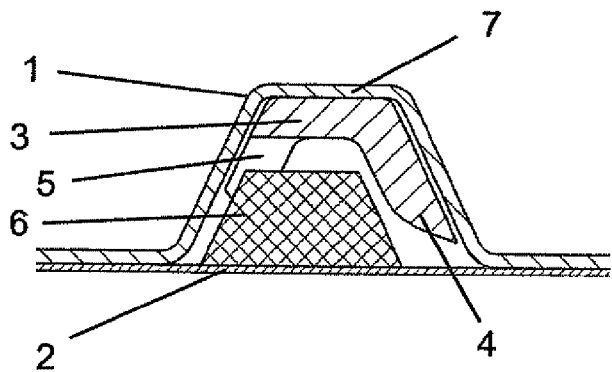
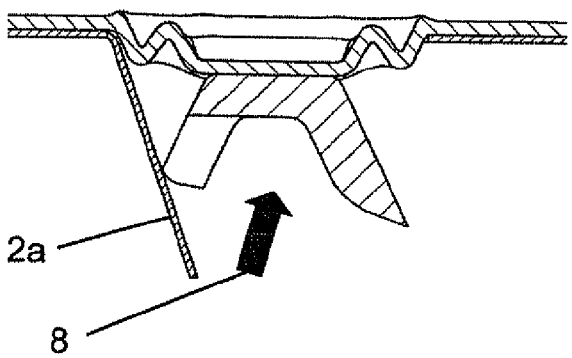
Fig. 1a
Fig. 1b
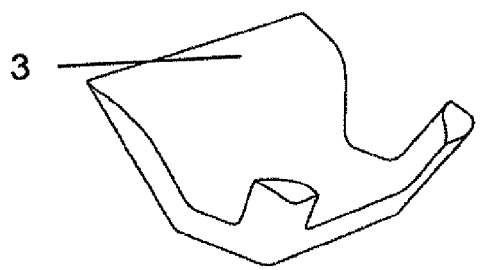
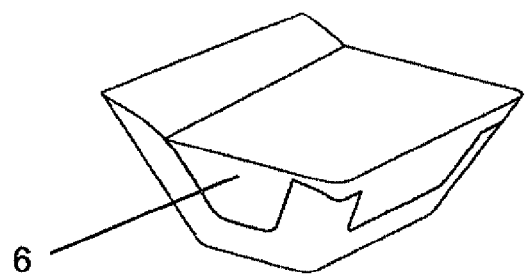
Fig. 1c
Fig. 1d
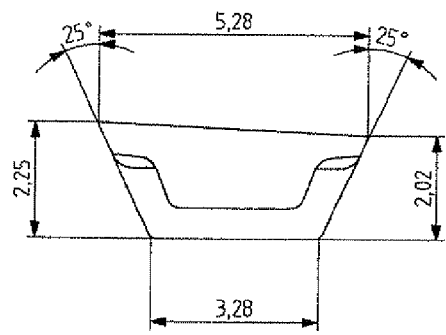
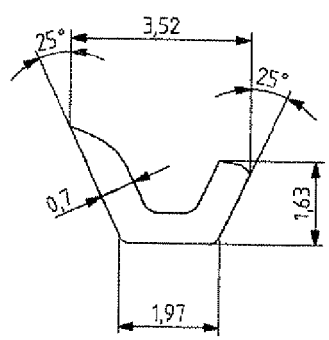
Fig. 1e

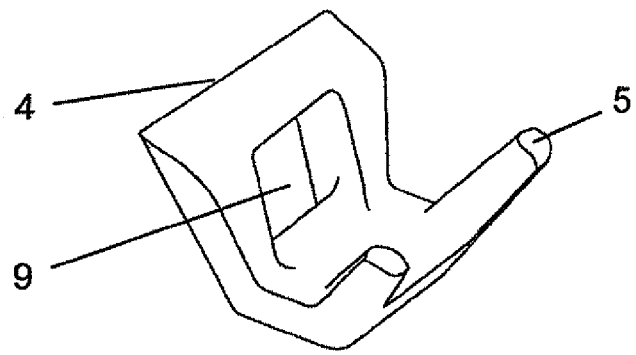
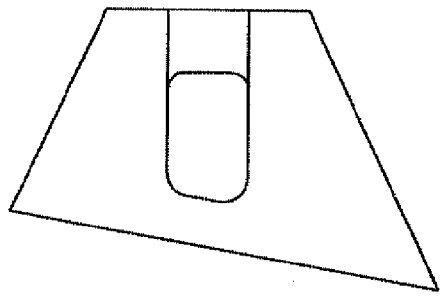
Fig. 2a                Fig. 2b
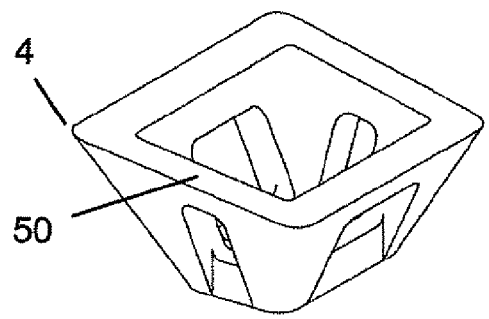
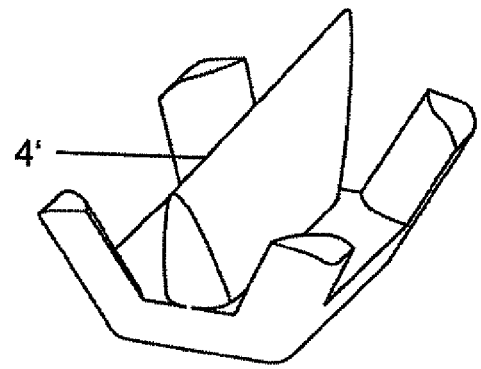
Fig. 2c                Fig. 3a
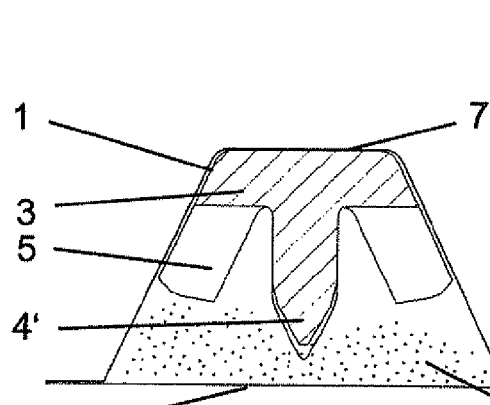
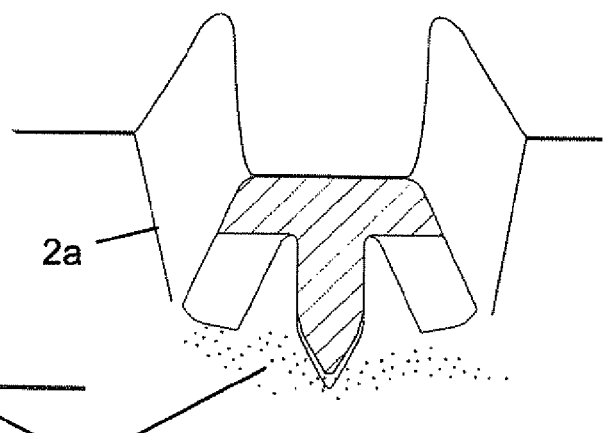
Fig. 3b
Fig. 3c

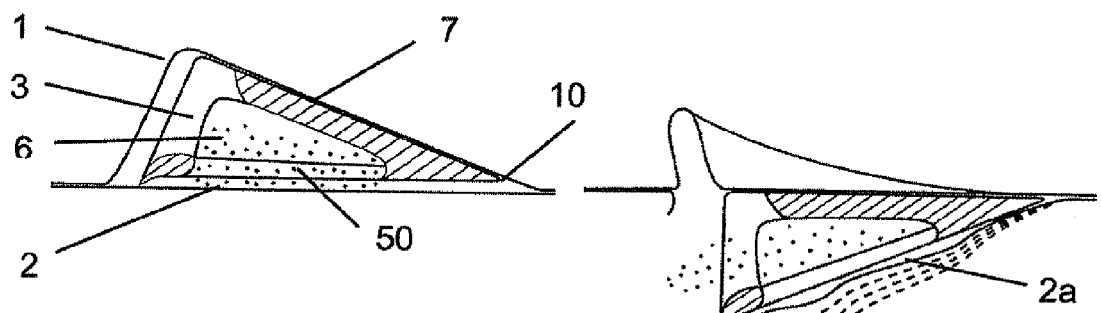
Fig. 4a
Fig. 4b
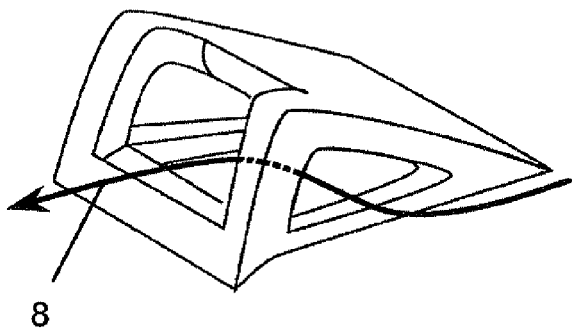
Fig. 4c
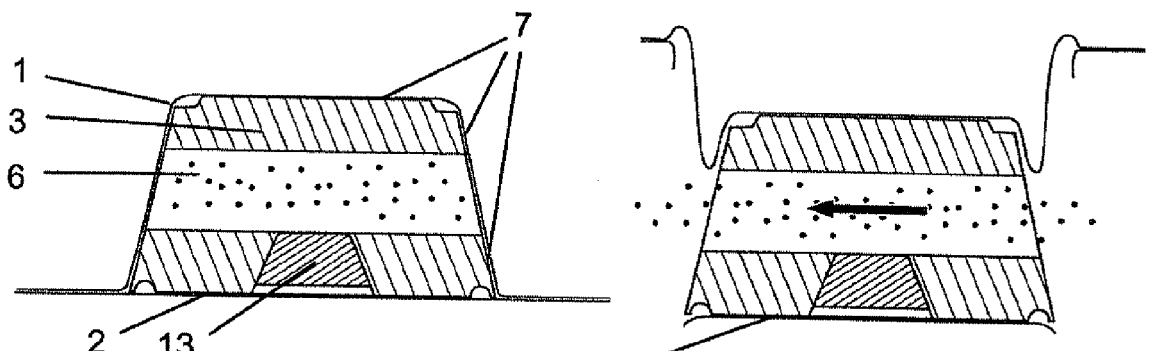
Fig. 5a
Fig. 5b

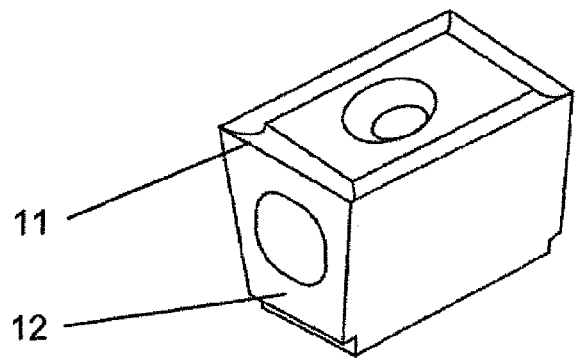
Fig. 5c
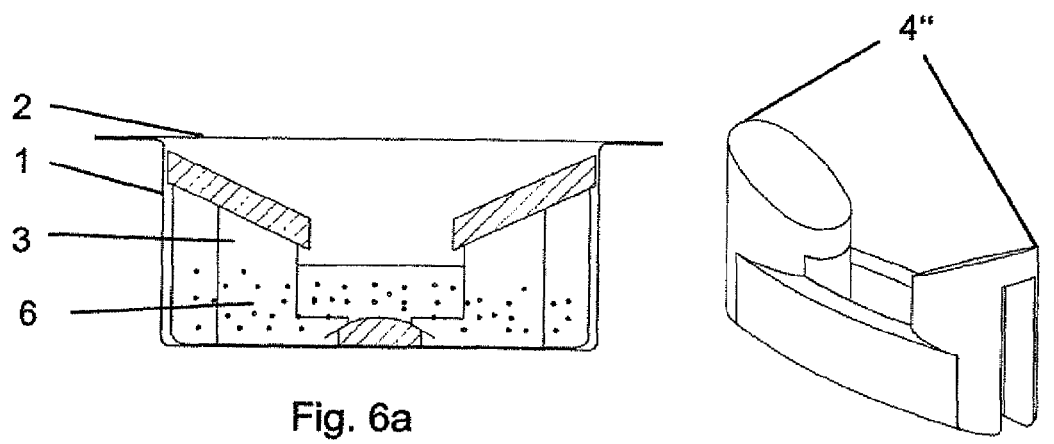
Fig. 6a
Fig. 6b
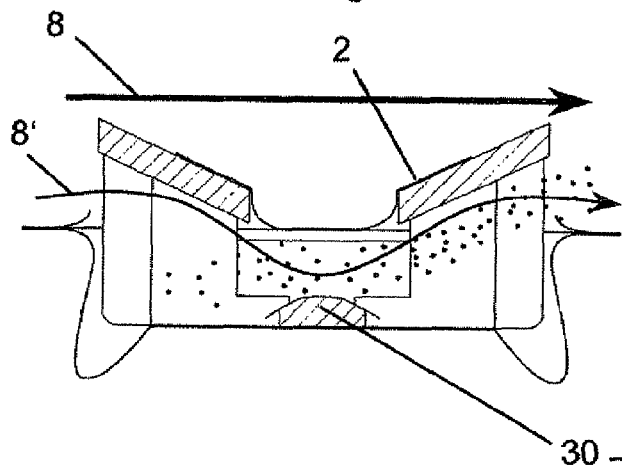
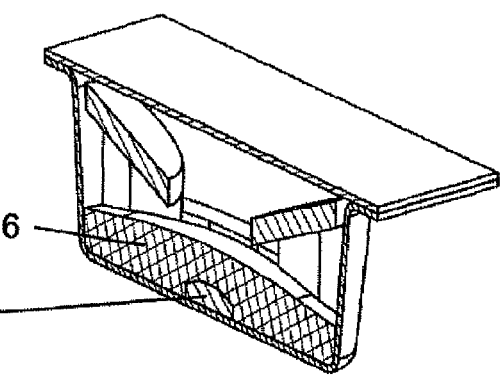
Fig. 6c
Fig. 6d

Figure 12A:
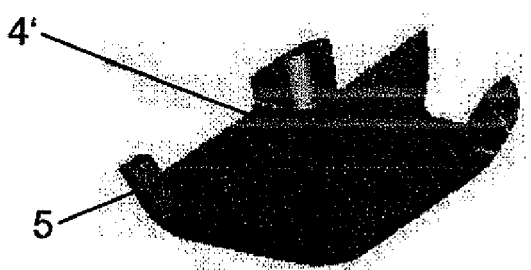
Figure 12B:
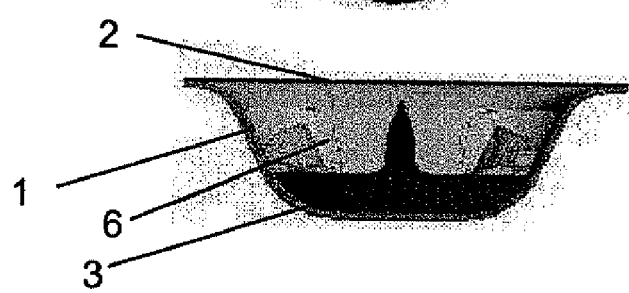

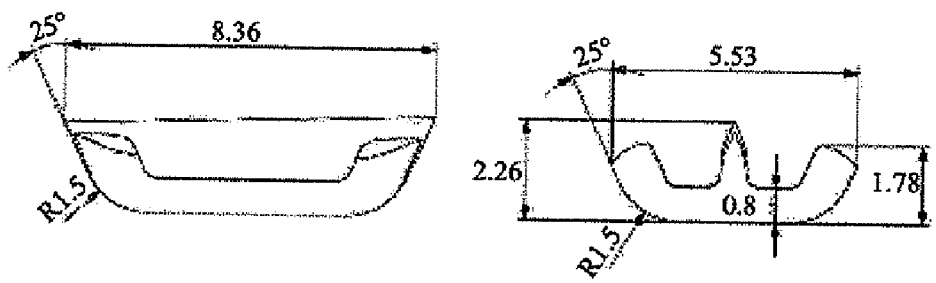
Fig. 12c
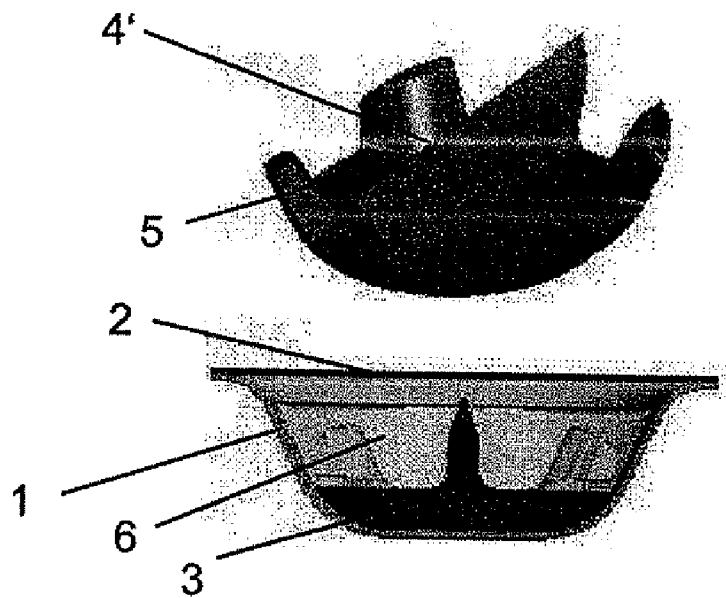
Fig. 13a
Fig. 13b
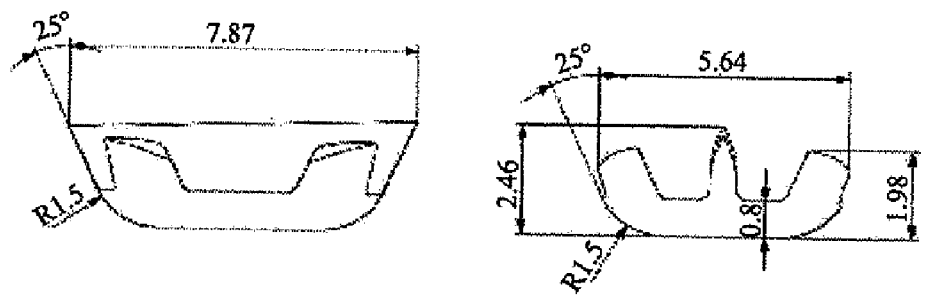
Fig. 13c

MEDICAMENTS MAGAZINE FOR AN INHALER, AND A MULTI-DOSE POWDER INHALER

This application is the national phase entry under 35 U.S.C. §371 of International Application No. PCT/CH2007/000180, filed Apr. 13, 2007, which claims priority to European Application No. EP 06405163.4, filed Apr. 13, 2006, each of which is hereby incorporated by reference in its entirety.

The invention relates to the field of medicament magazines, particularly to a medicament magazine for an inhaler and a multi-dose powder inhaler according to the preamble of the independent claims.

With medicament magazines the problem arises as to how to open a medicament chamber in which there is a medicament. Particularly for medicament magazines in inhalers there is a requirement that with medicaments in powder form these should not be compressed either during storage or during opening, so that no compacting of the powder takes place. In addition, an inhaler should be as simple, convenient and space-saving as possible in its design.

DE 44 00 083 describes a blister in which an individual medicament chamber has a spike or bump on the inside. By pressing on the back of the medicament chamber, a covering foil is pierced by the spike. If the spike or bump is also integrated in a half-well, the compacting of the powder can be reduced to some extent. However, during pressing out, the well is deformed, so that any powder located adjacent to the spike is still compacted between the well and the foil. Moreover, the tearing off of the covering foil is not clearly defined, on account of the spike, the bump or an encircling convexity of the foil. On the one hand, this creates the risk that torn off pieces of foil will get into the medicament, and on the other hand, because of the imprecisely defined opening of the medicament chamber, the reproducibility of an amount of medicament to be delivered is not guaranteed, as residual amounts of powder may remain behind an incompletely torn away foil.

The device disclosed in U.S. Pat. No. 6,082,358 is intended to guarantee the reproducibility of individual doses of medicament. For this purpose, a transfer element is inserted in a medicament chamber of a blister. A force exerted on the reverse side of a blister is transferred, by means of this transfer element, onto the entire length of a blister covering foil without compressing the powder contained in the transfer element. The covering foil then tears open along the entire length of the chamber. The transfer element with the powder contained therein is subsequently pressed out of the blister into a removal channel.

The transfer element is typically a cylindrical element. The covering foil is torn open therewith. Even with a transfer element provided with a rib, the covering foil is torn open and cut open in a manner which is not clearly defined. To ensure that no flaps of foil extend into the removal channel, the transfer element is pushed correspondingly far out. The loose transfer elements are retained in the removal channel. Thus, each medicament chamber has its own separate removal channel associated with it in which the used transfer elements remain. They may optionally be collected in a collecting container. A construction of this kind takes up a great deal of space. It is also very complex to manufacture and maintain, as not just a blister but a whole unit has to be replaced.

US 2004/0206773 also discloses a foil blister in which a powdered medicament is protected from compaction. For this purpose a blister has a dish-shaped element in which the medicament is held. Pressing on the reverse side of the blister causes the edge of the dish, which is optionally chamfered or provided with piercing points, to penetrate the covering foil and the dish together with the medicament is pushed out of the blister. The dish thus moves into a removal channel. In addition, the emptying of the dish is made more difficult, depending on the direction of the incoming air flow and the position of the dish, as the air flow cannot enter the dish completely.

It is therefore an aim of the invention to provide a medicament magazine for an inhaler which makes it possible to have a simple opening mechanism in an inhaler and wherein a powder contained in the magazine is essentially not subjected to any mechanical loading when the chamber is opened.

These aims are achieved by the medicament magazines with the features of the corresponding independent patent claim. Preferred embodiments are defined in the dependent claims.

The medicament magazine according to the invention is intended for use in an inhaler, preferably in a multi-dose powder and comprises at least one medicament chamber. The magazine is formed from two foil strips arranged against one another, e.g. sealed together, the at least one medicament chamber being formed between the foil strips. A powder carrying an active substance may be contained in the medicament chamber. The medicament chamber then has an internal structure which is preferably a separate element, for example a plastics part produced by injection moulding or thermoforming.

In one embodiment of the invention the internal structure comprises, on a front end, a means for opening one foil strip. At the same time the medicament chamber also comprises a retaining device which holds the internal structure on the medicament magazine after the medicament chamber has been opened and ensures that the internal structure does not fall out or drop down and lie loose in a device, for example. A retaining device of this kind is preferably produced by attaching the internal structure to a foil, or by configuring the internal structure in such a way that it lies on a foil or parts thereof during or after the opening of the chamber. The use of a retaining device not only prevents the internal structure from getting into an inhalation channel, for example, but also makes it very simple to arrange for an internal structure to be guided back into an area for further transporting a blister, which may be necessary. For example, by simply raising a blister strip or a medicament magazine, the strip including the internal structure is moved out of a removal channel and can be moved along with a strip.

The internal structure comprises on the inside a space for accommodating a powdered medicament. This inner space or the entire medicament chamber is stabilised against mechanical influences from the outside by the internal structure.

The medicament magazine has the advantage that even in a foil blister a powder is protected from compression and hence compaction. Thus, very thin and flexible foils can be used to produce the foil blister. This in turn affects the storage space in an inhaler, in that for the same circumference a magazine can be provided with a larger number of single doses, or a magazine can be accommodated in an inhaler in a more compact and versatile manner. Depending on the embodiment, however, a foil can still be very stable and firm and may contain, for example, depressions provided therein beforehand for accommodating the internal structures.

These internal structures may also support external piercing mechanisms such as hollow inhalation needles, by acting as a centring and piercing aid and thereby stabilising a blister. The internal structure may be provided with opening means such as piercing points or cutting edges, or may assist in opening a medicament chamber by means of the shear surface. In the case of medicament chambers which are opened directly by means of an internal structure, the internal structures preferably also have cutting edges and/or piercing points.

One advantage of an internal structure that is used for actually opening a medicament chamber is that no external opening mechanism such as a piercing needle, a cutting edge, etc., is used more than once. This contributes greatly to a more hygienic use of a so-called multi-dose device. Nor is there any need for an additional reel for rolling up a detached foil or an additional reservoir for waste, as a medicament magazine has substantially the same circumference or the same shape before and after use, but with an opened, empty chamber.

An opening mechanism itself can be made simpler by essentially providing one element which exerts pressure on the reverse side of the magazine in the region of a medicament chamber. Depending on the design of the internal structure, the chamber can also be opened simply by rolling over a reverse side of a chamber. This simplifies the structure of an inhaler by the fact that a pressure mechanism of this kind does not need to be as accurate as a piercing mechanism, for example. As a result of these properties, an inhaler can be correspondingly cheaper and smaller in construction.

It is also possible to create internal structures which have different medicament fill openings and removal openings from one another. A fill opening is preferably large and arranged opposite a sealing foil that is to be applied. One or more removal openings that do not align with the fill opening and which are located in particular on a different side of the internal structure offer a wide range of options in terms of, for example, the structure of an inhaler, the dosing and nature of a medicament, etc.

In a preferred embodiment an internal structure is produced, preferably in one piece, by injection moulding. However, it is also possible to form the internal structures from other materials, e.g. by stamping, particularly from metal foils. The internal structure is mounted, after production, on a foil of a foil blister, preferably sealed thereon or injected directly onto the foil It is also possible to produce a foil together with its internal structure in one piece.

For a space-saving arrangement of individual blisters in a medicament magazine, particularly in a strip-shaped medicament magazine, the internal structures preferably have a rectangular outline. Depending on whether the space is required across the width or length of a medicament magazine, an internal structure may be very long and narrow, or rather more square. If demands are made of the material by the manufacture of the blisters, e.g. the forming of wells in a blister foil, the internal structures are correspondingly adapted to the conditions, e.g. they are shaped as rounder forms.

The medicament magazines are introduced into an inhaler in preferred embodiments in such a way that an internal structure is pressed out directly into an inhalation channel. If the pressing is carried out downwards, a powder falls out of the opened medicament chamber under the effect of gravity. In both cases the powder is carried along by an air current in the inhalation channel, e.g. by a person breathing in through the inhaler, while in the former case the air current detaches the powder directly from the internal structure. An air current of this kind may also have an assisting effect in the latter case.

On the one hand the internal structure is designed so as to prevent compacting of the powder when a blister is pressed open. On the other hand it is designed to be sufficiently open so that an air current can flow through the internal structure, preferably from several sides. This allows total emptying of the internal structure and hence reproducibility of a specified amount of medicament. A plurality of inlet and outlet openings for an air current or recesses on different sides of an internal structure may also increase the turbulence so as to assist with the disaggregation of active substance and carrier material.

The materials used for producing medicament magazines, particularly for foils and internal structures, are preferably pharmaceutically permitted materials. The films used may be multi-layer films, which are also suitable for the production of conventional blisters. These are usually multi-layer films having a layer of PE, PP or PVC and an aluminium layer. Depending on the particular requirement, the film is constructed, for example, to be more stable, e.g. as a base foil or blister, tear-resistant, e.g. as a peelable film, or capable of being pierced or pressed out, e.g. as a press-out foil, and this is done, for example, by the incorporation of a PET layer.

In preferred material combinations, an outermost layer (innermost, relative to the blister) of a first foil to which an internal structure is attached comprises the internal structure itself and an innermost layer of a second (covering) foil has the same material. The advantage of this is that all the sealing processes, such as the sealing of the inner structure to the first foil and the covering foils to the base foil, can be carried out by welding/fusing the same materials. The internal structures are then preferably made from PE, PP or PET, corresponding to the foils used.

It is also possible to use sealing lacquer, e.g. heat-sealing lacquer. This gives rise to more material combinations of the individual elements of a medicament magazine. A sealing lacquer may, for example, be applied to the covering and internal structure or to a base foil.

For sealing, heat is applied to the corresponding points which are to be welded or sealed. This can be done by various methods, e.g. by heat punches or by induction, while the aluminium layer may serve as the induction layer and releases heat to the surrounding plastics layer, which may be constructed as a separate lacquer coating, as an integrated layer of lacquer film or as a film coating. It is also possible to pre-heat the internal structure.

As a rule, covering foils are thinner than base foils, so that heat can be applied from outside, e.g. by means of a hot punch, very directly through a covering foil.

The medicament magazines are preferably used in a multi-dose powder inhaler. The number of single doses accommodated in the magazine is preferably in the range from 1 to 100 or up to 200 single doses, preferably in the range from 1-60, for example between 7-180 or 14-150, e.g. 30-120, 45-100, 30, 90, 60, 120. For inhalers, the maximum number of single doses is preferably 60, for reasons of convenience and therapy.

Typical multidose powder inhalers are known for example from U.S. Pat. No. 5,590,645, U.S. Pat. No. 4,627,432, U.S. Pat. No. 6,655,381 or WO 2005/002654. These describe all kinds of medicament magazines, e.g. in the form of strips or annular magazines, fixed or flexible, with integrated or separate medicament pouches and correspondingly different opening mechanisms such as piercing or peeling, in various combinations.

The blisters according to the invention with an internal structure are preferably used in multidose powder inhalers of this kind. The medicaments used and described in these publications are examples of the nature, composition and powder size of powders and medicaments that can be used in the blisters according to the invention. The inhalers mentioned in the specifications are also, in their size, application and general construction, inhalers of a kind that are suitable for the medicament magazines according to the invention, apart from the actual opening mechanism.

The pharmaceutically active substances, substance formulations or mixtures of substances used may be any inhalable compounds, such as e.g. inhalable macromolecules, as disclosed in EP 1 003 478. Preferably, substances, substance formulations or mixtures of substances which are taken by inhalation are used for treating respiratory complaints.

The compounds specified below may be used in the apparatus on their own or in combination. In the compounds specified below, W is a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the apparatus accin. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide
5-[2-(5,6-diethyl-indan-2-ylamino)-1-hydroxy-ethyl]-8-hydroxy-1H-quinoline-2-one
4-hydroxy-7-[2-{[2-{[3-(2-phenylethoxy)propyl]sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-on
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1.1 dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
[3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-adamantan-2-yl-2-(3-{2-[2-hydroxy-2-(4-hydroxy-3-hydroxymethyl-phenyl)-ethylamino]-propyl}-phenyl)-acetamide, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

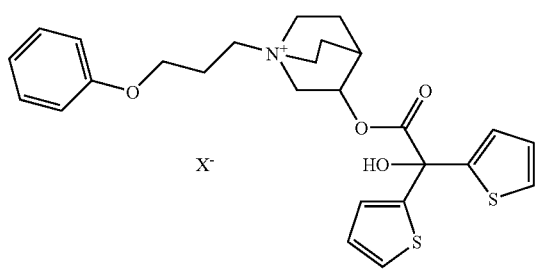

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-ene

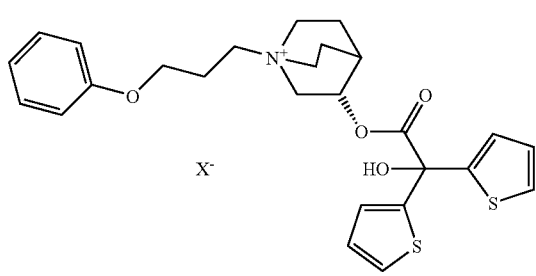

AC-1-ene wherein $X^-$ may have the above-mentioned meanings. Other preferred anticholinergics are selected from the salts of formula AC-2

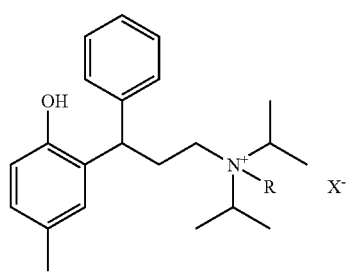

AC-2 wherein R denotes either methyl or ethyl and wherein $X^-$ may have the above-mentioned meanings. In an alternative embodiment the compound of formula AC-2 may also be present in the form of the free base AC-2-base.

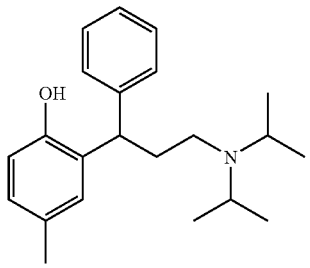

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for $X^-$.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325, 366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3 (3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxyethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethansulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline
optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Besides, inhalable macromolecules may be used, as disclosed in EP1 003 478.

In addition, the compound may from the group of the derivatives of ergot alkaloids, triptanes, CGRP-inhibitors, phosphodiesterase-V inhibitors, optionally in the form of the racemates, enantiomers or diastereomers thereof, optionally in the form of the pharmacologically acceptable acid addition salts, solvates and/or hydrates thereof.

Examples of ergot alkaloid derivatives are: dihydroergotamine, ergotamine.

Examples of substances suitable for inhalation include medicaments, medicament formulations and mixtures containing the above-mentioned active substances, and the salts and esters thereof and combinations of these active substances, salts and esters.

Figures 7A, 7B:
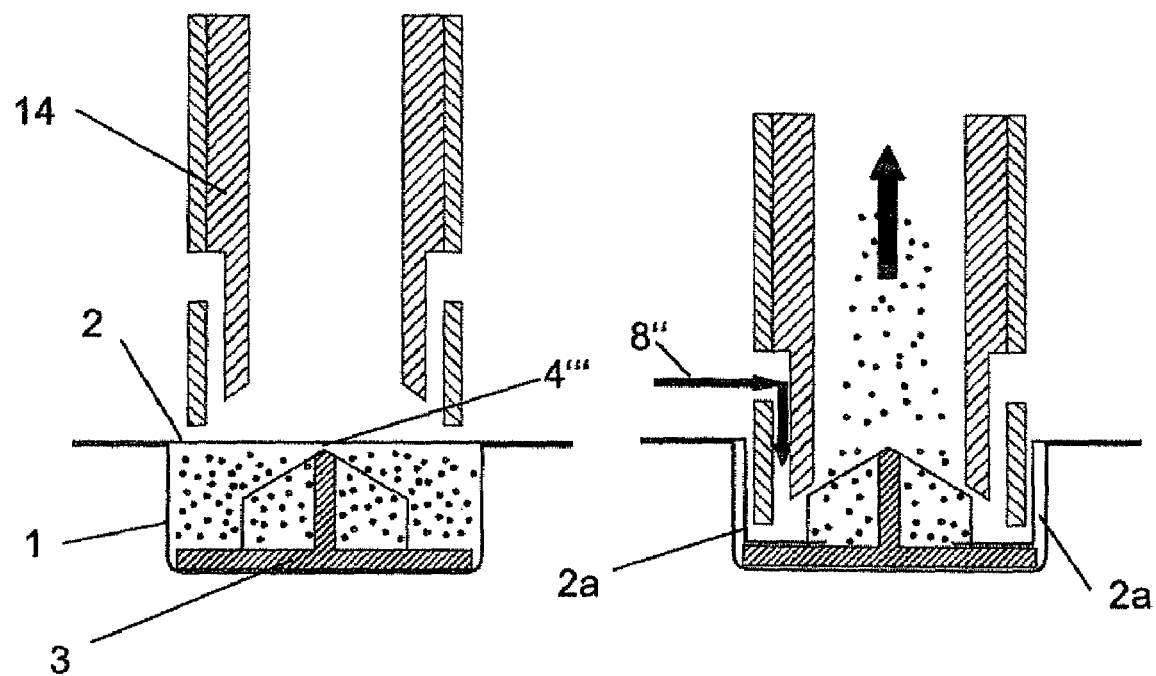
Figures 8A, 8B:
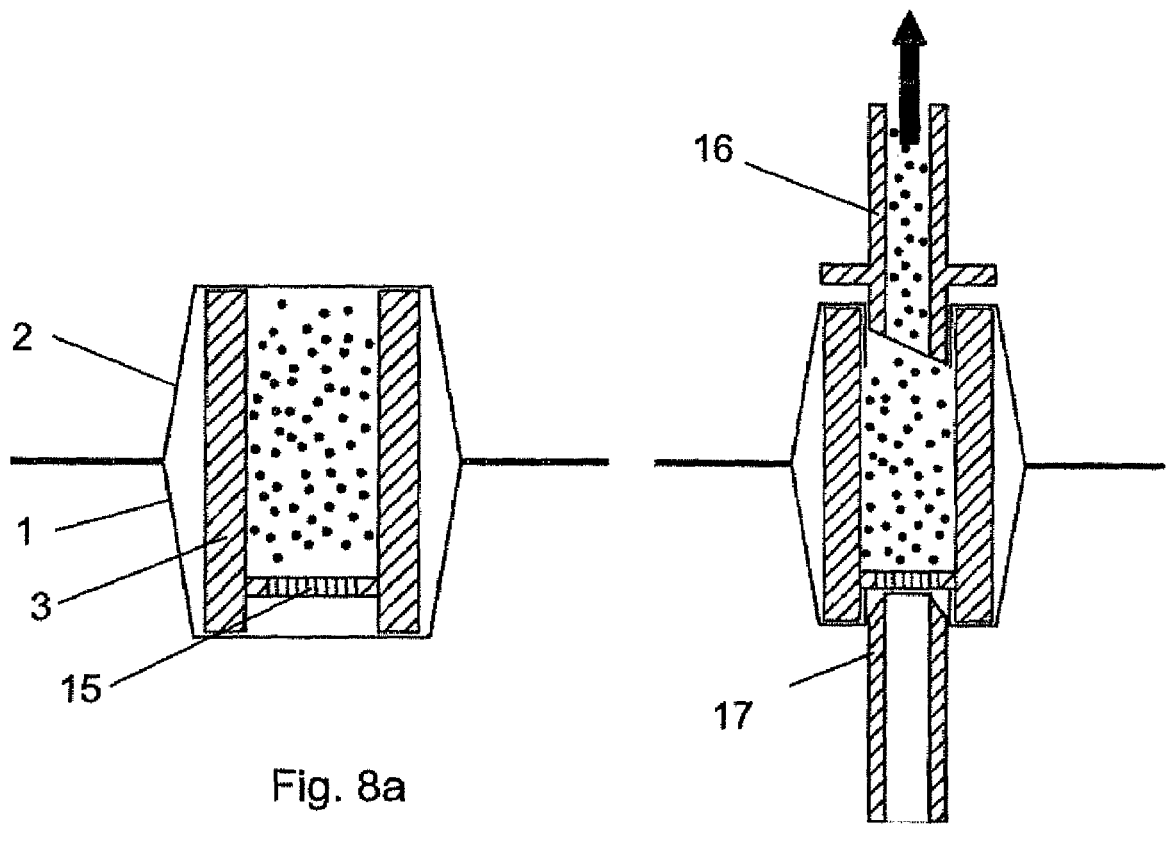
Figure 9A:
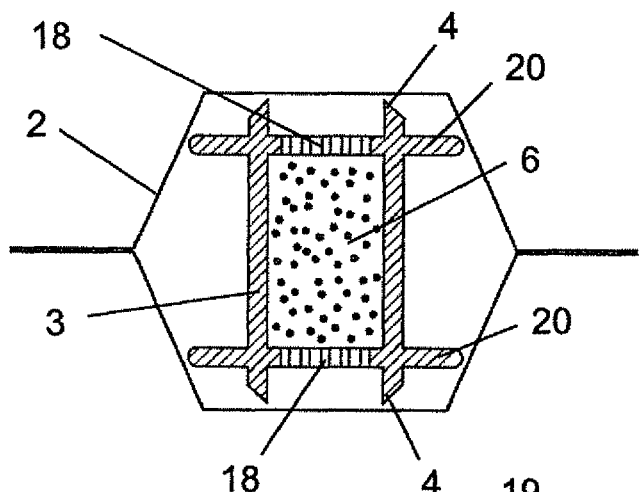
Figure 9B:
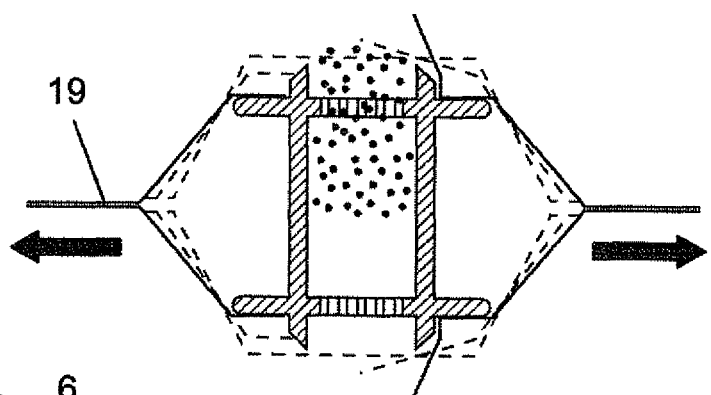
Figure 10A:
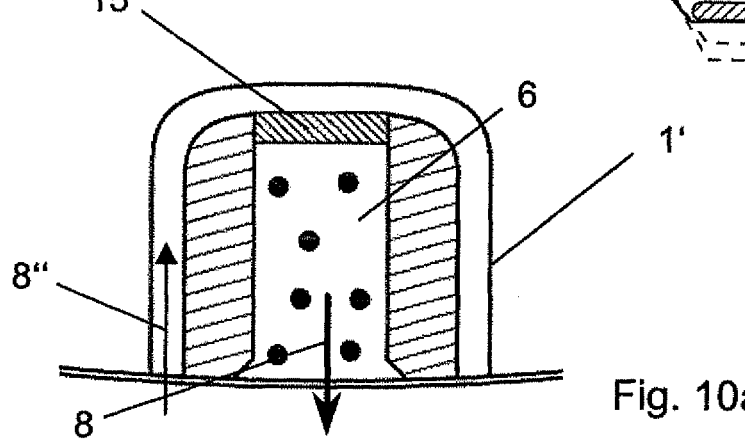
Figure 10B:
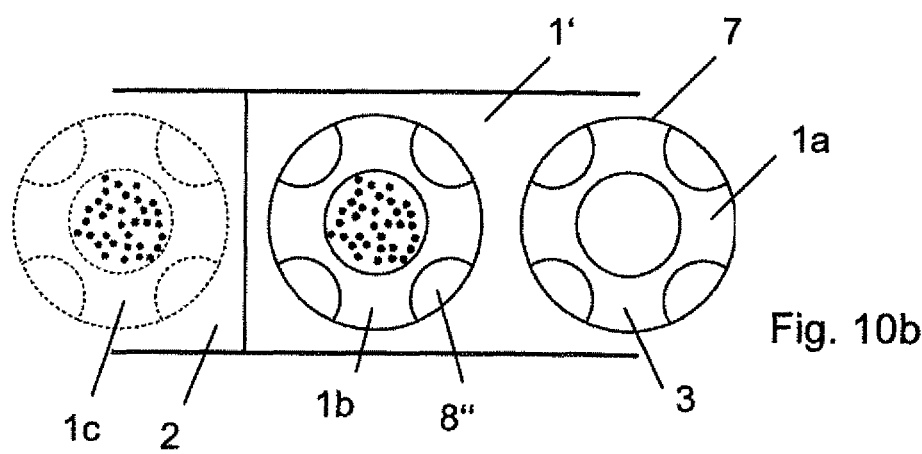

The object of the invention is explained in more detail hereinafter by means of preferred embodiments which are shown in the attached drawings. These drawings diagrammatically show:

FIG. 1a-1e a foil blister with internal structure,

FIG. 2a-2c other internal structures,

FIG. 3a-3c a foil blister with a symmetrical internal structure,

FIG. 4a-c a foil blister with an asymmetrical internal structure,

FIG. 5a-5c an internal structure with an air current through the inside of the internal structure, FIG. 6a-6d another internal structure with an air current through the internal structure, FIG. 7a, 7b an internal structure as a centring and piercing aid for suction needles, FIG. 8a, 8b another internal structure as a centring and piercing aid, FIG. 9a, 9b an internal structure with two-sided piercing points or cutting edges, FIG. 10a, 10b an internal structure with lateral air supply channels.

Figure 11A:
Figure 11B:
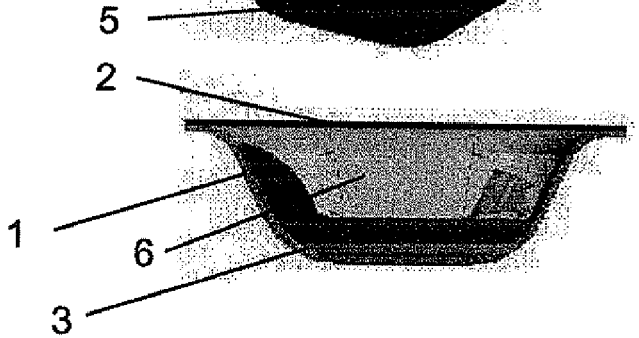
Figure 11C:
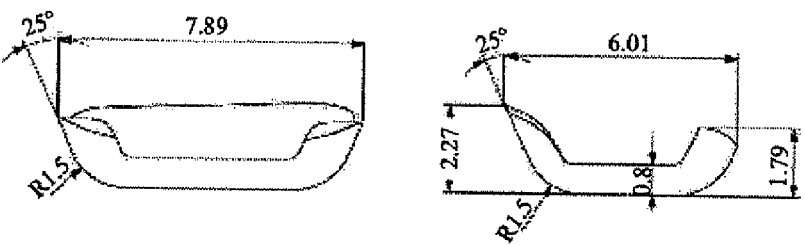
Figure 14A:
Figure 14B:
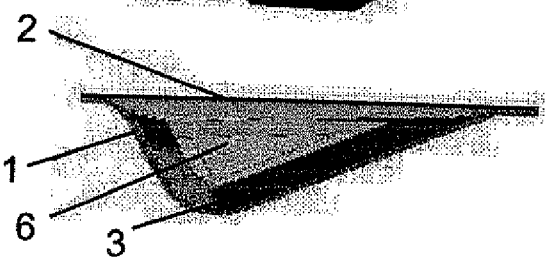
Figure 14C:
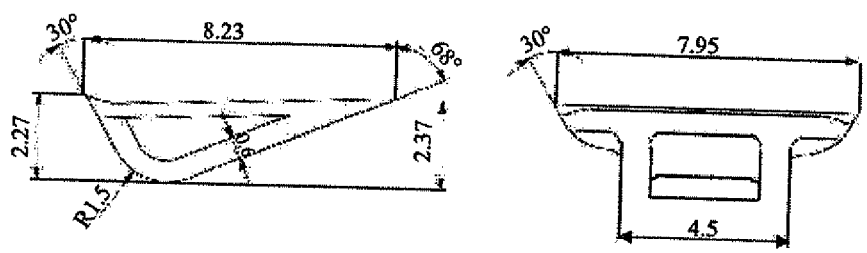

FIG. 11a-c a variant of the internal structure according to FIGS. 1a-e,

FIGS. 12a-c, 13a-c two variants of the internal structures according to FIGS. 3a-c, FIGS. 14a-c a variant of the internal structure according to FIG. 4a-c, FIGS. 15a-c blister shapes for internal structures according to FIGS. 11a-c, 12a-c and 13, and according to FIG. 14a-c.

Basically, in the Figures, similar parts have been given the same reference numerals. The medicament magazines described by way of example in the form of a foil blister each have a lower and an upper foil between which is provided an internal structure. In the Figures a first lower foil is the one in which the internal structure is incorporated and which for this purpose generally has a depression, or as a result a depression is formed therein. The second foil is correspondingly designated a sealing foil, as it is applied in a manufacturing process to form a seal over a filled internal structure or medicament chamber. Depending on the material and manufacturing process of the magazine the two foils are arranged symmetrically. The medicament chambers are preferably parts of a medicament magazine with a plurality of medicament chambers arranged side by side, containing single doses of medicament.

FIG. 1a shows a section through a medicament chamber in a foil blister. The blister has a first foil 1, an internal structure 3 and a sealing foil 2 tightly connected to the first foil 1. The internal structure 3 has a side wall with a cutting edge 4 and, on the side opposite the cutting edge, two legs 5 (FIG. 1c). The legs 5 are set back relative to the cutting edge 4 and assist the opening process of the medicament chamber. If a force acts on the reverse side of the blister, first the cutting edge 4 is pressed against the sealing film 2, cutting it open. Then the legs 5 press the foil flaps 2a which have previously been opened by the cutting edge to one side, as shown in FIG. 1b. The powder 6 contained in the blister can now fall out and/or be removed from the blister by an air current 8, indicated by an arrow in the Figure. An air current can flow through the internal structure from above, between the side wall and the pressing legs, but may also enter the internal structure sideways.

The internal structure is sealed on its reverse side by the first foil. This has the advantage that the internal structure cannot fall down and/or become a separate part even when the blister is fully open. With this type of blister, moreover, no material is produced that has to be collected separately. The internal structure can also additionally be sealed on the longitudinal sides of the internal structure, so that no powder 6 can get behind these side wall portions.

The internal structure 3 also has a certain stability, so that the powder 6 contained therein is wholly or partly protected from external mechanical influences, particularly compaction caused by pressure.

FIGS. 1d and 1e show a diagonal view and two side views including a dimensioning of the internal structure by way of example for a powder volume of about 10 mm³, taken as an example. The Figures also show that the cutting edge is slightly inclined, so that the sealing foil is pierced by a corner of the cutting edge at the start of the opening process and only subsequently is it cut open along the entire width of the internal structure, along the cutting edge. It would also be possible to replace the cutting edge with a piercing point and a cross-member. The foil would still be pierced at one corner, but the remaining width of the foil would not be cut open in a controlled manner, but torn open.

A variant of the internal structure according to FIGS. 1a-e is shown in plan view, lateral sectional view and as a section to scale. In this variant, various edges and elements are rounded off or have larger radii. This allows an improved airflow through the internal structure. The altered radii at the legs also prevent a sealing foil from starting to tear at the legs. The generally flatter and wider variant also allows a higher fill capacity. The volume of the internal structure according to FIG. 1e given by way of example is about 10 mm³, whereas the variant according to FIG. 11c has a maximum fill capacity of about 40-45 mm³.

Round outer shapes for the internal structure are also preferred for a magazine or a blister, depending on the manufacturing process. For example, simple deep-drawing methods may be used to shape blister structures, without exceeding elastic limits for multi-layer foils containing aluminium, for example (cf. also FIGS. 15a-c). The blister shapes can thus be made rounder, while a corresponding internal structure is then preferably matched to the round structures of the blister.

FIGS. 2a, 2b and 2c show further examples of internal structures with a lateral cutting edge and a substantially rectangular or square outline. FIG. 2a also comprises two push-up legs 5. The side wall that contains the cutting edge 4 comprises an opening and a resultant cavity 9. This opening ensures that the amount of powder that might possibly get behind the side wall is as small as possible: powder can get back through the opening into the inner space of the internal structure and is not trapped between the side wall and foil.

In the internal structure according to FIGS. 2b and 2c the legs are constructed as corner pillars which are joined together by cross-members 50 and are connected to the cutting edge. The cross-members allow a controlled cutting or pressing up of the sealing foil, depending on whether the cross-members are additionally formed as cutting edges. The internal structure also has different heights at different corners, so that the opening of the sealing foil starts at one corner and extends in controlled manner over the following edges or cross-members.

In the embodiments according to FIG. 2a-c an air current can flow longitudinally and transversely through the internal structure. This also produces turbulence currents which assist with the disaggregation of a medicament from a carrier powder.

FIGS. 3a to 3c show a symmetrical internal structure 3 with a centrally arranged cutting edge 4' and a corresponding opening process for a blister. The internal structure, shown here in the interests of simplicity with a substantially rectangular or square outline, has a cutting edge over its entire width. In addition, four legs 5 slightly set back relative to the cutting edge are mounted at all four corners as additional opening aids.

The powder 6 contained in the blister is protected from pressure by the space which is braced by the cutting edge and legs. The blister is in turn sealed on its reverse side with one foil 1, while the sealing foil 2 keeps the blister closed. If the blister is opened by the effect of force on its reverse side, the cutting edge 4' cuts through the sealing foil, and two foil flaps 2a are formed with the aid of the legs 5. These foil flaps 2a are shorter than they would be with a lateral cutting edge and thus reduce the risk of becoming detached, left hanging or getting in the way during the powder removal process. The sectional drawings in FIGS. 3b and 3c again show the cutting edge which is raised on one side. Because of the seal 7 on the reverse side of the internal structure, this remains attached to the first foil.

A symmetrical shape for the internal structure has the advantage of making manufacture and handling easier. An internal structure of this kind in which the central cutting edge essentially severs the internal structure is preferably introduced into an inhalation or removal channel in such a way that an air current is formed parallel to the cutting edge. The lateral recesses between the legs assist or even make possible an airflow perpendicularly to the cutting edge.

A preferred retaining device is a seal attaching the internal structure to a foil. However, the internal structure may also be attached in some other way than to a foil, for example mechanically, e.g. in the form of a rivet or press stud. The internal structure has, on its rear side which is to be mounted on a foil, a structure which can be clamped to a corresponding form of an external structure. One foil of a blister is trapped between the internal structure and the external structure. External structures of this kind are preferably an integral part of a medicament magazine and may have other functions, depending on their design: If a medicament magazine is in the form of a strip, external structures may be used for example as guides for the strip; they may be used directly for an opening mechanism in which pressure is exerted on the magazine and hence on the internal structure via the external structure; they may be used as an index for indicating a magazine position, etc.

Mechanical, preferably clamping retaining means of this kind are advantageous when a seal is not possible or desirable or if additional functions such as those mentioned above, for example, are to be integrated in a medicament magazine.

Two variants of the internal structure according to FIGS. 3a-c are shown in FIGS. 12a-c and 13a-c, in each case in plan view, in lateral sectional view and as sections drawn to scale. These variants are in turn characterised by their rounded-off edges and leg radii. The substantially square or rectangular base surface of the internal structure allows alignment thereof when the structure is placed in or onto a first foil In FIGS. 13a-c the base surface of the internal structure is almost totally rounded. A completely round base or end surface makes it possible for example to place an internal structure in a pre-shaped first foil, as there is no need for any alignment, but such alignment would be achievable, with difficulty.

FIGS. 4a to 4c show a blister with an internal structure which is on the one hand asymmetrical and in addition to a seal 7 on its reverse side also permits a different type of retaining mechanism. The internal structure in this embodiment essentially has the lateral cross-section of a right-angled triangle, this cross-section enabling the blister to be opened by pressing on its reverse side. Because of the ramp-like triangular shape of the reverse side of the internal structure it is possible to apply pressure parallel to and along the foil blister (which runs from right to left in the plane of the drawing). This can very easily be carried out by rolling over it, e.g. with a roller subjected to pressure, over the reverse side of the blister. It is also possible for a blister strip to be "pressed out" during further transportation on a ramp-shaped element, for example (the strip would be moving from left to right). In this way a device may be made more compact, as for example there is no need to lift a force-applying element.

As a result of the force acting on the inclined reverse side of the blister, a cutting edge 4 located on the front of the internal structure 3 cuts into the sealing foil 2 and buries itself further in the manner of an excavator shovel. Cross-members 50 which extend from the cutting edge substantially parallel to the sealing foil 2 and are preferably also in the form of cutting edges cut the sealing foil along its entire length and lead to an elongate foil flap 2a. If the internal structure is pressed totally out of the blister or the medicament chamber, the powder contained in the internal structure falls into an inhalation chamber (not shown) at least partly under the effect of gravity. It is also possible for the powder to be additionally loosened from the internal structure by an air current 8 acting in the inhalation chamber, as indicated by an arrow in FIGS. 4b and 4c. The foil flap 2a may have an assisting function in detaching the powder, in that the flap 2a vibrates under the effect of the air current 8 against the underside of the internal structure, and thereby causes the powder to be knocked out. A movement of the foil flap 2a is shown by dotted lines in the Figure. Lateral openings and a front opening in the internal structure allow an air current 8 to pass through the internal structure, as shown in FIG. 4c. This ensures total detachment of the powder and turbulence to improve the detachment of an active substance from a carrier material (dispersion).

To prevent the internal structure from falling out of the blister, a kind of hinge 10 may be formed by foil(s) and internal structure, instead of or in addition to the seal 7 on the reverse side of the internal structure on the first foil. The internal structure 3 is pressed out of the blister by a rotary movement. In order to form a hinge 10 of this kind, for example, the edge of the internal structure at which the hypotenuse and the adjacent side of the triangle meet could be extended so that the edge is firmly held, e.g. stuck, welded or sealed, between the two foils.

The internal structure shown in FIGS. 4a-4c would also be suitable for being formed from a metal foil, e.g. by stamping and folding.

Not only the pressing out of the internal structure can be made very compact in this embodiment. The returning of the internal structure onto a plane in the non-pressed-out state of the blister, for example for the purpose of further conveying a blister strip, may be carried out by pressing the internal structure onto a ramp-like element, for example. As a result, a number of actions may take place simultaneously as the blister strip is conveyed onwards: the transporting and returning of the internal structure to its original position, and possibly also the pressing out of a new blister.

In this Figure a typical direction of movement of a blister strip also corresponds to a direction of removal, possibly in the opposite direction. In preferred embodiments of an inhaler, a removal will take place substantially perpendicularly to the direction of movement of a medicament magazine, for reasons of space.

A variant of the internal structure according to FIGS. 4a-c is shown in FIGS. 14a-c, in plan view, lateral sectional view and as a section drawn to scale, respectively. In this embodiment, the reverse side in particular and the corners and edges of the base surface of the internal structure are rounded off. In addition, the base surface is wider than the reverse side. The internal structure forms, behind an opened foil, a frame for a powder or generally pressure-sensitive medicament contained therein. Here, too, the cutting edge is slightly inclined relative to the foil which is to be cut, so that the foil is pierced at individual points to begin with and the cut upon in a controlled manner along the cutting edge.

FIGS. 5a and 5b show a section through a blister 1 with a box-like internal structure 3. The box has a fill bore 13 in the centre of a front side for the introduction of a powder 6, which is closed off with a stopper after filling. The internal structure is arranged between two foils such that an upper sealing foil 2 closes off the fill bore, so that the stopper may be omitted if desired. The powder 6 introduced is then preferably located entirely in a channel inside the internal structure. This channel extends along the internal structure and is connected to the fill bore 13.

Cutting edges 11 which extend along the front side and around the internal structure, cf. FIG. 5c, cut a hole in the sealing foil 2 that corresponds to the area of the internal structure. Because of a seal 7 on the front side of the internal structure the section of foil cut out remains attached to the internal structure. The opened blister is now preferably positioned such that the internal structure is located in an inhalation channel. An air current in the inhalation channel, indicated by an arrow, leads through the channel in the internal structure and carries the powder 6 contained therein with it. The sealing foil 2 on the internal structure 3 and/or the stopper prevents powder from escaping anywhere other than through the openings in the channel, the outlet openings.

An additional seal 7 is also provided between the first foil and the reverse side of the internal structure, to prevent the internal structure from falling off the foils. However, a seal 7 for the first foil 1 may also be provided on those sides of the internal structure that contain the outlet openings. As a result, no powder gets outside the internal structure into the medicament chamber. The lateral seals are detached from the internal structure during the opening process of the blisters, thereby exposing the outlet openings.

In the embodiment of the internal structure described, a powder is totally protected from compression during storage but also when the blister is opened. In addition, a fill opening that is independent of one or more outlet openings allow more clearance for the purpose of removal or dosing of a medicament. These are determined essentially by the outlet openings, generally by the resistance to removal from the internal structure. However, a fill opening is preferably as large as possible, so that filling can be carried out quickly and easily. In addition, a fill opening should be on an upper side of a blister, whereas removal openings, as in the present case, may be arranged on the side, depending on the inhaler arrangement.

Another embodiment that has a fill opening independent of outlet openings in an internal structure is shown in FIGS. 6a to 6d. A powder 6 is again introduced through a fill opening lying opposite the sealing foil 2. Openings on the reverse and sides are closed off with a first foil, while the lateral openings are detached from the foil 1 during the opening operation and expose a passage through the internal structure for air to flow through. FIG. 6b shows an air current 8 passing over the structure, and a deflected air current 8' leading through the internal structure. FIG. 6c shows two arcuate cutting edges 4" which cut two spaced-apart openings into the sealing foil 2. When the internal structure is pressed out of the blister, the sealing foil is pressed against the internal structure in an intermediate region between the cutting edges (cf FIG. 6b), so that on the one hand the fill opening is closed off and on the other hand the internal structure is held in the blister without having to seal off a reverse side. The internal structure has a turbulence element in the powder region which provides additional turbulence during the removal of the powder and thereby helps to break up clumps in the powder.

FIGS. 7a, 7b, 8a and 8b show internal structures which, in addition to having a stabilising function, are also piercing and centring aids for suction needles, cannulas, air supply needles, etc., which are to be introduced into the blister 1 from outside.

In FIGS. 7a and 7b the internal structure 3 is substantially symmetrical and has a centrally arranged piercing point or a cutting edge 4'''. The internal structure 3 is shown in combination with a double cannula 14. The double-walled cannula is designed so that suction can take place through its interior (arrow shown in bold type) while the air supply 8" is guaranteed through the outer part. The internal structure consists of a plate which has roughly the same diameter as the cannula 14. In the centre of the plate, walls are provided that converge conically towards the centre and which act as guides or abutment points for the cannula to be introduced. For this purpose the walls have a diameter which is slightly greater than the internal diameter of the cannula.

The internal structure is applied to the first foil 1, which may be pre-formed, by injection moulding, sealing or some other method. Preferably as the internal structure is applied a corresponding depression is formed in the foil 1. Then the still open medicament chamber is filled and sealed off with a sealing foil 2. During the piercing with the cannula 14 the sealing foil is pierced and torn or cut open in the centre of the blister by the internal structure as a result of the force acting on it. The free lateral foil flaps are pressed down by the double cannula to the side, into the medicament chamber and onto the plate of the internal structure. An air current 8' can now flow through the cannula, through the internal structure or past the internal structure from the outside, and on the inside it can be guided along the cannula in the direction of suction, thus making it possible to remove substantially all the powder.

The internal structure 3 in FIGS. 8a and 8b does not itself have any piercing points or cutting edges. The internal structure consists essentially of a tube or of two parallel walls of the same size which are joined together by a filter 15 at the lower end. The internal structure is preferably a plastics component and the filter 15 is an integral part thereof, which is essentially a thin plastics wall provided with filter openings. The filter prevents the powder contained in the blister from getting into a device or prevents undesirable small parts from entering the chamber through an air supply needle 17 (see below).

The internal structure is designed for use with a suction 16 and air supply needle 17. For this purpose, the two foils are pierced from above and below, the suction and air supply needle having a corresponding cutting edge or piercing points. The diameter of the tube is such or the two walls of the internal structure are at such a spacing from one another that the needles 16, 17 can be introduced between them. When the foils 1, 2 are cut open, the resulting foil flaps are pressed to the side between the needle and foil or wall, where they seal off the needles and medicament chamber from one another.

Whereas the air supply needle 17 is located at the filter, the suction needle 16 preferably has a retaining mechanism, e.g. an annular rim around the suction needle 16, which is provided at the walls of the internal structure and allows a specified degree of penetration of the suction needle into the internal structure.

Instead of the two walls or the tube, the internal structure could also be a rectangular cylinder, so that a medicament contained therein is essentially totally enclosed. Round shapes are preferred for the internal structure, as their manufacture, centring of a needle or their alignment with the foil are easier. The upper and lower foil may be sealed onto the internal structure.

FIGS. 9a and 9b show a round or angular cage-like internal structure 3, which is not sealed to a foil. As the retaining mechanism to prevent the internal structure from falling out or dropping down after the opening of the blister, it comprises projections 20 outside the actual internal structure containing the space for the powder. The inner space is in turn braced by a round cylinder, two parallel walls or a rectangular cylinder. The walls or cylinder have, at their ends, piercing points or cutting edges 4 which sever the upper and lower foils 2. Between the walls or inside the cylinders are formed, preferably integrally, screens which hold back coarser particles in the inner space.

The projections are arranged outside the upper and lower cutting edges 4 and are in the form of extensions to the screens 18.

FIG. 9a shows a blister in the unopened state while FIG. 9b shows one in the opened state. This blister may be opened by pulling laterally on the tabs 19 in the direction of the arrow. Various stages of the opening operation are shown in FIG. 9b by dotted foil positions.

FIGS. 10a and 10b show an internal structure 3 with a plurality of air supply channels. A powder 6 is contained in the cylindrical inner space of the substantially cylindrical internal structure. The inner cylinder is provided with a filter 15 on one side, so that no foreign bodies can get into a powder through the air supply 8'' and thereby enter an inhalation channel. FIG. 10b shows a plan view of a blister strip 1' with three medicament chambers at various stages of use. One medicament chamber or blister 1a is empty, the internal structure still being in the blister strip 1', for example as a result of a seal 7 attaching the side walls of the internal structure to the blister strip 1'. A second blister 1b is open and ready for dispensing the powder. A third blister 1c is still sealed off by a sealing foil 2.

The channels for the air supply may also be set into the internal structure on the filter side, in such a way that even pressing a rear foil cannot affect the channels or interfere with the air supply.

The medicament chamber may be opened by pulling, peeling off or piercing the foil in the region of the openings.

An internal structure shown in this Figure stabilises a medicament chamber and protects the powder contained therein from being compressed. However, the powder is removed without pressing the internal structure out of the foil. The blister strip 1' can therefore be a very thin, soft foil, as the medicament chamber is stabilised by the internal structure, and in particular the air channels are kept open by the internal structure. Conversely, it is also possible to use a very stable foil which might be unsuitable for pressing out. This would make it possible, for example, to mould this foil into a shape that can help to hold the air supply channels open by virtue of its stability.

Figure 15A:
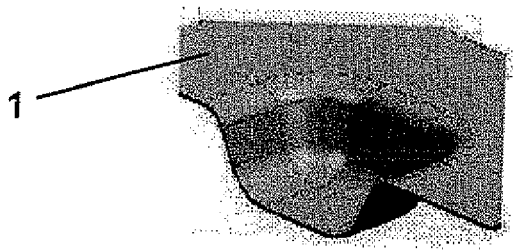
Figure 15B:
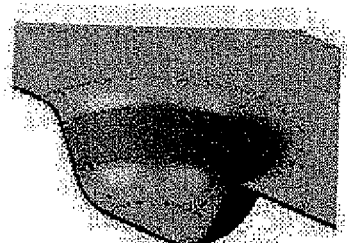
Figure 15C:
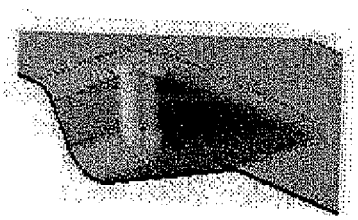

FIGS. 15a-c show blister shapes by way of example into which different internal structures can be introduced. The blister shape according to FIG. 15a is suitable, for example, for the internal structure according to FIGS. 11a-c and 12a-c, the blister shape according to FIG. 15b for the internal structure according to FIGS. 13a-c and the blister shape according to FIG. 15c for the internal structure according to FIG. 14a-c.

The blister shapes may be produced by various methods. Deep-drawing and thermoforming methods are particularly suitable.

Depending on the foil used, elastic limits of the material must be observed during the manufacturing process. Lower elastic limits can be compensated by rounder shapes for the internal structures. In the examples given, this is the case with the internal structures according to FIGS. 11-13. Critical points are (examples of values for the internal structures in FIG. 11-13 are given in brackets): maximum possible radii (1.5 mm), clear coating angle on the wall (25°), ratio of width to depth (>2.7).

Sealing tests were carried out for internal structures on foils. It was found that very good results were obtained with commercially obtainable foils for pharmaceutical products. In particular, different multi-layer foils which are also used in the manufacture of conventional blisters were used for the tests. The covering foils (press-out and pull-off foils) have different thicknesses of aluminium ranging from 20-40 μm. In addition, foils with PVC or PP layers combined with heat-sealing lacquer and foils with polymer layers (LDPExtr) were used. The base foils used, which are theoretically more stable than covering foils, had an aluminium layer in the range from about 45-47 μm and a polymer layer (oPA) of about 25 μm. The base foils differ essentially by a layer of PVC, PP or PE using for sealing. The thicknesses of the PVC and PP layers were in the region of 60 μm, whereas PE layers were about 40 μm thick.

The invention claimed is:

1. Medicament magazine having at least one medicament chamber for use in an inhaler, wherein the magazine is formed from two foil strips applied to one another, and the at least one medicament chamber is formed between the foil strips,
    wherein the medicament chamber has an internal structure (3), this internal structure comprises on the inside a space for accommodating a powdered medicament and stabilises this inner space against mechanical influences from the outside, and wherein
    the internal structure comprises, on a front side, means for opening one foil strip
    characterised in that a retaining device is provided in the medicament magazine which holds the internal structure against the medicament magazine after the opening of the medicament chamber,
    wherein the internal structure (3) has at least one protruding piercing point or cutting edge (4, 4', 4'', 4''') and protruding opening aids that are set back relative to the piercing point or cutting edge
    wherein two parallel cross-members (50) extend at an inclined angle from the side wall comprising the cutting edge (4) or the piercing point to the side of the internal structure (3) opposite the side wall.

2. Medicament magazine having at least one medicament chamber for use in an inhaler, wherein the magazine is formed from two foil strips applied to one another, and the at least one medicament chamber is formed between the foil strips,
    wherein the medicament chamber has an internal structure (3), this internal structure comprises on the inside a space for accommodating a powdered medicament and stabilises this inner space against mechanical influences from the outside, and wherein
    the internal structure comprises, on a front side, means for opening one foil strip
    characterised in that a retaining device is provided in the medicament magazine which holds the internal structure against the medicament magazine after the opening of the medicament chamber,
    wherein two parallel cross-members (50) extend at an inclined angle from the side wall comprising the cutting edge (4) or the piercing point to the side of the internal structure (3) opposite the side wall,
    wherein the opening aids are constructed as individual legs (5) arranged at a spacing from the at least one cutting edge (4,4',4'',4''') and/or as cross-members (50) between the at least one piercing point or cutting edge and other parts of the internal structure (3), and
    wherein the cross-members (50) are formed as cutting edges (4).

3. Medicament magazine having at least one medicament chamber for use in an inhaler, wherein the magazine is formed from two foil strips applied to one another, and the at least one medicament chamber is formed between the foil strips, wherein the medicament chamber has an internal structure (3), this internal structure comprises on the inside a space for accommodating a powdered medicament and stabilises this inner space against mechanical influences from the outside, and wherein the internal structure comprises, on a front side, means for opening one foil strip characterised in that a retaining device is provided in the medicament magazine which holds the internal structure against the medicament magazine after the opening of the medicament chamber, wherein the internal structure (3) has at least one protruding piercing point or cutting edge (4,4',4",4"') and protruding opening aids that are set back relative to the piercing point or cutting edge wherein the internal structure (3) is of asymmetrical construction and the cutting edge (4) is formed by a side wall of the internal structure or the piercing point is part of a side wall of the internal structure, wherein the cross-members (50) are connected at one end to the side wall and at the other end to a rear wall of the internal structure (3) or to ends of legs (5) mounted on the rear wall.

* * * * *